United States Patent [19]

Dickhudt et al.

[11] 4,411,276
[45] Oct. 25, 1983

[54] IMPLANTABLE MULTIPLE CONNECTOR

[75] Inventors: Eugene A. Dickhudt; Roger A. Paulson, both of New Brighton, Minn.

[73] Assignee: Medtronic, Inc., Minneapolis, Minn.

[21] Appl. No.: 258,259

[22] Filed: Apr. 28, 1981

[51] Int. Cl.³ ............................................. A61N 1/04
[52] U.S. Cl. ................................................ 128/784
[58] Field of Search ............. 128/419 P, 784; 339/60, 339/61, 75 RM, 256 S, 119 R, 120, 122 F, 125, 252 P, 259 R; 46/1 R; 24/115 N

[56] References Cited

U.S. PATENT DOCUMENTS

| | | | |
|---|---|---|---|
| 869,686 | 10/1907 | Bauno | 46/1 R |
| 983,258 | 1/1911 | Bliss | 339/75 M |
| 1,657,253 | 1/1928 | Fortin | 339/256 S |
| 2,183,067 | 12/1939 | Gardner | 339/252 P |
| 2,393,083 | 1/1946 | Wisegarver | 339/256 S |
| 2,427,001 | 9/1947 | Hubbell et al. | 339/256 S |
| 2,711,331 | 6/1955 | Temple | 24/115 N |
| 2,840,676 | 6/1958 | King | 339/60 R |
| 3,058,083 | 10/1962 | Schneider | 339/256 S |
| 3,124,405 | 3/1964 | Massa | 339/75 M |
| 3,253,595 | 5/1966 | Murphy | 128/405 |
| 3,440,333 | 4/1969 | Blomstrand | 339/256 S |
| 3,760,332 | 9/1973 | Berkovits | 339/66 R |
| 3,924,921 | 12/1975 | Feightner | 339/252 P |
| 4,112,953 | 9/1978 | Shanker | 128/419 |
| 4,142,532 | 3/1979 | Ware | 128/419 |
| 4,236,525 | 12/1980 | Sluetz | 128/419 |
| 4,332,259 | 6/1982 | McCorkle, Jr. | 128/786 |

FOREIGN PATENT DOCUMENTS 821722  5/1937  France ............................ 339/259 R

*Primary Examiner*—William E. Kamm
*Assistant Examiner*—Mitchell J. Shein
*Attorney, Agent, or Firm*—Robert J. Klepinski; John L. Rooney; Joseph F. Breimayer

[57] ABSTRACT

A body implantable connector for connecting a plurality of implantable devices, such as connecting an extension to a lead. There is a sheath having two open ends, one of which frictionally fits over the end of the lead and the other of which fits over the end of the extension. The sheath is of pliant material of sufficient strength to resist breaking under the forces normally exerted on the connector, but sufficiently pliable to deform and to contract about the lead and the extension under the frictional forces created between the sheath and the lead, and the sheath and the extension when the lead and the extension are urged in a direction tending to separate them. A wire extends longitudinally within the sheath and mates with lumens in the conductors of the lead and the extension to make electrical connection between the lead and the extension. There is a member within the sheath, intermediate the open ends of the sheath, and integrally formed with the sheath which supports the wire within the sheath. A stop is attached to the wire to prevent it from pulling through the support member.

8 Claims, 5 Drawing Figures

IMPLANTABLE MULTIPLE CONNECTOR

BACKGROUND OF THE INVENTION

1. Field of the Invention

The invention in general relates to the field of implantable connectors for making physical and electrical connection to and between implantable leads, and more particularly, concerns an improved connector that permits a lead and an extension to be joined at any point along their length, and which provides a dynamic gripping action that permits a positive connection without the use of set screws, adhesives, etc.

2. Description of the Prior Art

In recent years, many devices have been developed which are designed for implantation in a body. For example, electrical tissue stimulators are now routinely implanted in humans for treatment of heartblock, pain, scoliosis, and other medical problems. Generally, an electrical lead is used with these devices to carry an electrical current or voltage from a pulse generator or other electrical device to the body part that needs to be treated. Such leads generally consist of a conductor encased in an insulator which is generally inert to body fluids. In many such leads, the conductor is in the form of a coil with a passage down the center of the coil called lumen. The conductor is made in this form because such coil conductors are extremely flexible and highly resistant to breakage; in addition the lumen permits the insertion of a stylet into the lead to stiffen the lead during implantation to allow it to be handled and placed more easily.

As the art of the implantable devices, and the leads for use with the implantable devices has developed, so also has the art of connectors for connections between the implantable devices and the leads developed. Conventional electrical connectors used in external applications generally are not suitable for use with implanted devices. Implanted devices must be highly reliable because the health and life of patients may depend on them for long periods, such as ten years or more, and because they cannot be replaced except by expensive and traumatic surgical procedures. In addition, such devices must be capable of such high reliability in a hostile environment—the human body—in which they are subject to much movement and flexing. For these reasons, up to now, such connectors have consisted of relatively complex positive fixation devices encased in protective materials. Perhaps the most common of such devices has been a pin socket type arrangement containing a set screw in the socket which can be screwed down upon the pin after the pin has been inserted to positively hold the pin in place, with the whole encased in protective medical-grade silicone or similar material. Such connectors tend to be significantly larger than the lead itself and thus add significant bulk to the implantable lead. The larger the implanted device, the more trauma it may cause the body, and thus it is desirable to have smaller connectors. One solution to this problem has been the use of medical adhesive to hold a pin and socket device together. While the use of the medical adhesive may solve some of the bulk problem, it has its own disadvantages, such as difficulty in making a disconnection without destroying the part if a disconnection is necessary, contamination of the site due to particles which become loose, failure of the adhesive under flexing, etc.

Conventional implantable electrical connectors have, up to now, required special fittings on the lead or other terminal which it is to be connected to, in order to ensure a positive fixation. Leads must be specially made in fixed lengths with the fittings attached. Since human bodies are of various sizes, this results in the necessity of stocking many different lengths of leads which is expensive and impractical, or the implanting of leads that are longer than necessary and the coiling of the excess length within the body. The excess length adds further bulk to the implanted material and provides additional opportunities for failure and trauma due to the presence and flexing of the superfluous lead length.

In certain situations in the art of implantable medical products it is necessary to connect two leads together, or as the terminology has developed in the art, to connect a "receiver extension" or an "extension" to a lead. This situation arises in the art of implanting stimulators to control pain as a result of the fact that whether or not pain can be successfully treated with this method varies from person to person and is dependent upon the site of stimulation and other feature. Thus, the typical procedure for such treatment is as follows: a small incision is made in the region of the site to be stimulated and a lead is inserted and the electrode placed at the stimulation site; stimulation is provided for a trial period which may last a number of days; if stimulation at the site is successful enough in controlling pain to warrant the implantation of a device, a receiver for receiving stimulation signal or a pulse generator for producing stimulation signals is then implanted in the body of the patient. Generally the receiver or pulse generator is placed in a location in the body which is comfortable, safe and cosmetically satisfactory, which location generally is away from the site of stimulation. Further, it is highly desirable to leave the originally implanted lead in place, since its effectiveness has been proven and it would be traumatic to remove it. Thus, a receiver extension or an extension is provided that extends from the point of implant of the receiver or pulse generator to the site of the original incision where it is connected to the original lead. Because of the variability in placement of the receiver or pulse generator and the variability in the placement of the stimulating electrode and because of the other factors peculiar to implantable devices discussed above, it is highly desirable to have a lead connector which is small in size, yet provides reliable positive fixation and, at the same time, provides for connection to both the extension and lead at any point along their length without the use of special adaptors.

SUMMARY OF THE INVENTION

It is an object of the invention to provide an implantable connector which is relatively small, and thereby provides minimum trauma upon implantation.

It is another object of the invention to provide such a connector which provides positive fixation without the disadvantages of the prior art.

It is a further object of the invention to provide an implantable connector which permits connection to leads, extensions, or other such electrical terminals at any selected point along their length, thus permitting the customizing of lead and extension length without the disadvantages of implanting excess lead or extension length or having to stock many different lengths of leads and extensions.

It is another object of the invention to provide a connector in which the portion of the connector which serves to physically connect the leads or terminals also serves to protect the region of connection from body fluids.

The invention provides a body implantable connector for connecting a plurality of terminals, each terminal including a conductor. The connector comprises a sheath means having a plurality of open ends for frictionally fitting about each of the terminals, the sheath means being of a pliant material having sufficient strength to resist breaking under the forces normally exerted on the connector, but sufficiently pliable to deform and contract about the terminals under the frictional forces created between the sheath means and the terminals when they are urged in a direction tending to separate them. The pliable material is preferably a material which is generally inert to body fluids. The connector also includes a means for making conductive connection between the conductors of the terminals.

Preferably the means for making conductive connection is a wire which mates into lumens within the conductors of the terminals. Preferably, there is a means for supporting the wire or other means for making conductive connection, which means for supporting is integrally formed with said sheath of the pliable material and is within the sheath, intermediate the two open ends of the sheath. Preferably there is a stop attached to the wire or other means for making conductive connection, which prevents the wire or other means from pulling through the support member.

The invention also contemplates a new method of connecting an implantable lead to a terminal including the steps of severing the lead at the point at which it is desired to make a connection and inserting said severed end and the terminal into the connector, thereby making physical and electrical connection between the terminal and the lead.

In the preferred embodiment there are two such terminals, and the terminals comprise the ends of a lead and an extension, with the conductor of the lead and extension being of the coil type having a lumen extending axially through the center of the coil into which the wire, or other means for making conductive connection mates.

Numerous other features, objects and advantages of the invention will become apparent from the following detailed description when read in conjunction with the accompanying drawings.

DESCRIPTION OF THE PREFERRED EMBODIMENT

Figure 1:
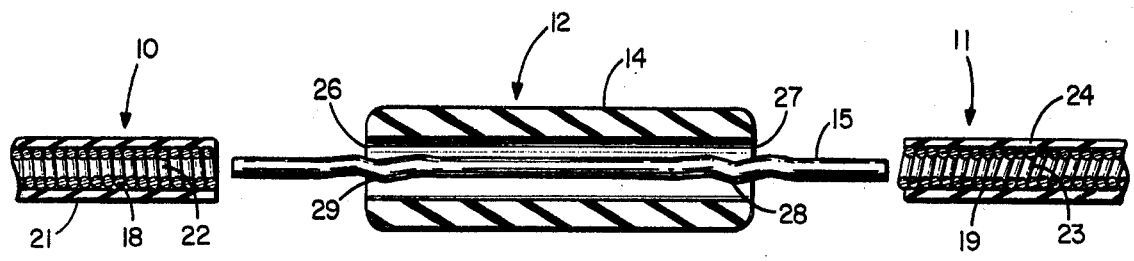
FIG. 1 is a sectional view of a connector according to the invention for connecting a lead and an extension, with the section being taken along the axis of the connector and the lead and extension.
Figure 4:
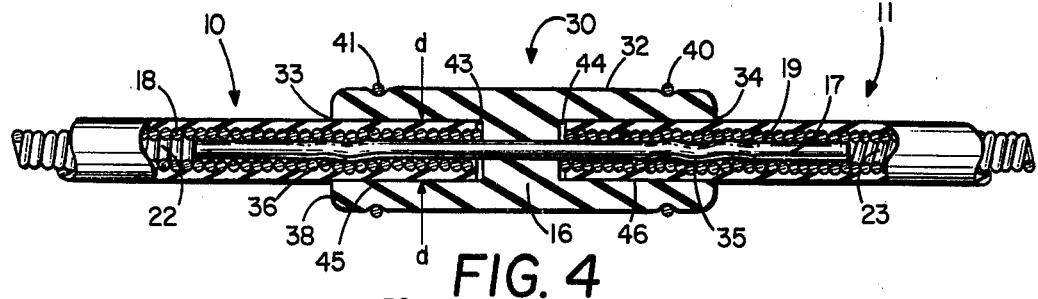
FIG. 4 is a partially cutaway and sectional view of the embodiment of the invention shown in FIG. 2 with the lead and extension inserted in the sheath and further employing sutures for assisting in fixing the sheath to the lead and extension.

Directing attention to FIG. 1, a lead 10 and an extension 11 are shown in position about to be connected by a connector 12 according to the invention. Connector 12 includes a sheath means 14 and a means 15 for making conductive connection between conductor 18 of lead 10 and conductor 19 of extension 11. In FIG. 4 a lead 10 and extension 11 are shown positioned within sheath means 32 in another embodiment of a connector 30 according to the invention. Sheath means 32 frictionally fits about lead 10 and extension 11 and is made of a pliant material having sufficient strength to resist breaking under the forces normally exerted on connectors 12 and 30, but sufficiently pliable to reform and contract about lead 10 and extension 11 under the frictional forces created between the sheaths, such as 32, and the leads 10 and extension 11, such as at point 45, when the sheath and leads are urged in directions tending to separate them. Thus, if forces are exerted, for example tending to pull lead 10 to the left (FIG. 4) and extension 11 to the right, the frictional forces between lead 10 and sheath 32, such as at 45, and the frictional force between extension 11 and sheath 32, such as at 46, will cause sheath 32 to stretch. The stretching of sheath 32 causes its diameter, such as at d—d in FIG. 4, to contract, further increasing the frictional forces between lead 10 and sheath 32 and lead extension 11 and sheath 32 sufficiently to prevent lead 10 and lead extension 11 from slipping out of connector 30.

Proceeding now with a more detailed description of the various embodiments of the inventions which are shown in the drawings, FIG. 1 shows an embodiment of a connector 12 according to the invention which is used in connecting between a lead 10 and an extension 11 which may, for example, be a receiver extension or other extension. Lead 10 comprises a coil conductor 18 encased in an insulator 21. Coil conductor 18 has a lumen 22 extending axially within it. Similarly extension 11 comprises a coil conductor 19 having an axial lumen 23 and encased in an insulator 24. Connector 12 comprises a sheath 14 and a wire 15. Sheath 14 is open at both ends 26 and 27. Wire 15 is bent to form several projections such as 28 and 29, which projections extends a distance greater from the axis of wire 15 than the radius of wire 15. Wire 15 has a diameter less than or equal to the diameter of lumens 22 and 23, and extends substantially longitudinally within sheath 14, that is, substantially along a direction parallel to the axis of sheath 14. "Substantially" here means near enough to a longitudinal direction that it will not block the openings 26 and 27 of sheath 12 preventing lead 10 and extension 11 from entering the opening. For example, the invention contemplates an embodiment in which wire 15 does not have bend such as 28 and 29 but is inclined slightly to the axis of sheath 12 so that it will contact the interior of coils 19 and 20 sufficiently to make good electrical contact, but not so much as to impede the slipping of lead 10 and extension 11 into sheath 14.

Figure 2:
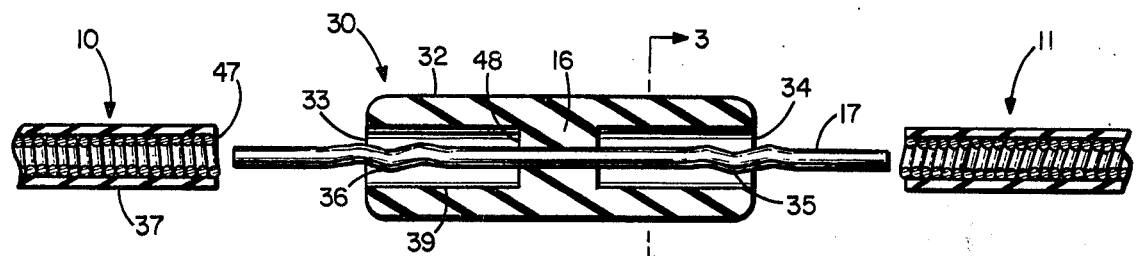
FIG. 2 is an axial-sectional view of another preferred embodiment of the invention, which includes a member for supporting the means for making conductive connection.

FIG. 2 shows a sectional view of an embodiment of the connector according to the invention which is the same as the embodiment shown in FIG. 1 except it includes a means 16 for supporting a means 17 for making conductive connection within sheath means 32. Again, in this embodiment, sheath means 32 is open at both ends 33 and 34 and the means for making conductive connection comprises a wire 17. Means 16 comprises a member integrally formed with sheath 32 and located intermediate the open ends 33 and 34 of the sheath 32.

Figure 3:
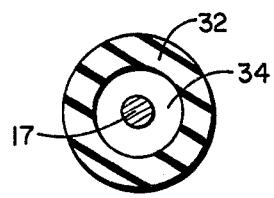
FIG. 3 is a cross-sectional view of the connectors of either FIG. 1 or FIG. 2 taken through the line 3—3 shown in FIG. 2.

FIG. 3 is a cross-sectional view of the embodiment of the invention shown in FIG. 2 and taken through lines 3—3 in FIG. 2. This view more clearly shows the cylindrical shapes of sheath 32, opening 34, and wire 17 in this embodiment.

FIG. 4 shows the connector 30 of FIG. 2 with lead 10 and extension 11 inserted within openings 33 and 34 respectively in sheath 32. Wire 17 has noted into lumens 22 and 23 within lead 10 and extension 11 respectively. The interior of conductors 18 and 19 contacts the projections 35 and 36 of wire 31, thereby making electrical connection between conductor 18 of lead 10 and conductor 19 of extension 11. Preferably the projections, such as 35 and 36 are slightly compressed in the interior of conductors 18 and 19 respectively, so that the contact between the projects 36 and 35 and the interior of conductors 18 and 19 is a firm one. It can be seen in this embodiment, that sheath means 32 protects the regions 43 and 44 of juncture between lead 10 and extension 11 and connector 30 so that body fluids cannot enter the juncture. Sheath 32 in this embodiment thus insulates and protects the electrical connection means 17 in addition to providing the function of making the physical connection between lead 10 and extension 11. In FIG. 4, sutures 40 and 41 have been tied about sheath 32 further compressing the sheath 32 about extension 11 and lead 10 respectively. A means such as sutures 40 and 41 for further compressing sheath 32 about terminals such as extension 11 and lead 10 is optional with the invention. That is, the connector according to the invention such as 30, would hold firmly to the lead 10 and extension 11 even without the sutures 40 and 41. However, since the conductor is generally used in medical situtations requiring the highest degree of safety, surgeons and others using the connector may desire to doubly ensure the integrity of connection by placing the means such as 40 and 41 about sheath 32.

Figure 5:
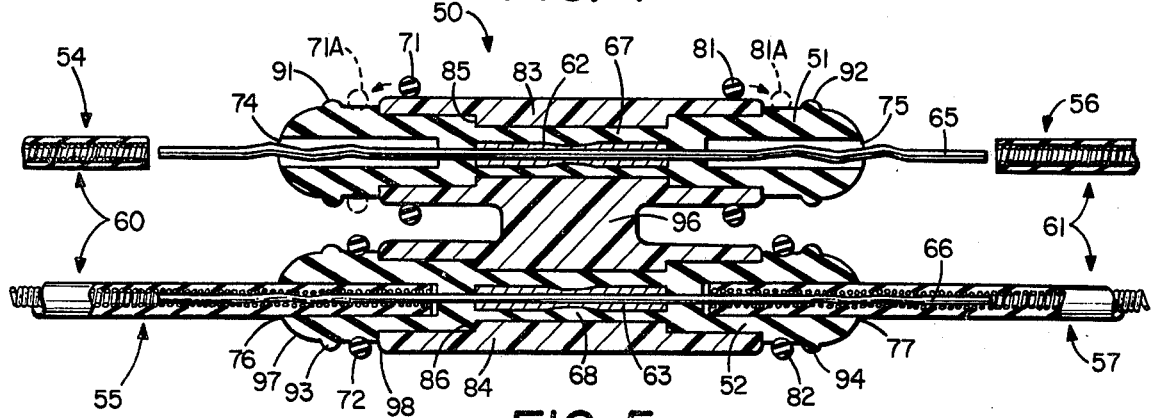
FIG. 5 is a sectional view of a connector according to the invention for making connection between bipolar leads and extensions and including O-rings for further assisting in connecting the sheath to the leads and extensions, and also including a stop for preventing the means for making conductive connection from pulling through the support member.

FIG. 5 shows another preferred embodiment of a connector according to the invention. In this embodiment, the invention may be employed to connect a bipolar lead 60, that is, a lead in which there are two conductors, to a bipolar extension 61. In addition, this embodiment includes a means such as 62 for preventing the means for making a conductive connection, such as 65, from pulling through the support member such as 67. Further, this embodiment incorporates O-rings, such as 71, as a means for further compressing the sheath 51 about lead 60 and extension 61. It is noted that the two lead portions 54 and 55 may come together further to the left than the termination point of the drawing to form an integral bipolar lead 60, and similarly, extension portions 56 and 57 come together further to the right than the termination point of the drawing to form an integral bipolar extension 61, or alternatively they each may be a pair of unipolar leads.

Turning now to a more detailed discussion of the embodiment of FIG. 5, connector 50 comprises a pair of sheaths 51 and 52 each having a pair of open ends 74 and 75 and 76 and 77 respectively. Connector 50 also includes a pair of wires 65 and 66 extending longitudinally within sheaths 51 and 52. Wires 55 and 56 are supported within sheaths 51 and 52 by members 67 and 68 respectively integrally formed within sheaths 51 and 52 respectively. Stops 62 and 63 prevent each of wires 65 and 66 from pulling through support members 67 and 68 respectively. In this embodiment stops 62 and 63 comprise sleeves crimped onto wires 65 and 66 respectively. O-rings 71 and 81 fit about the open end 74 and 75 of sheaths 61, while O-rings 72 and 82 fit about the open ends 76 and 77 of sheath 52. Rigid sleeve 83 encircles sheath 51 while rigid sleeve 64 encircles sheath 52. Each of rigid sleeves 83 and 84 includes a flange 85 and 86 which prevents the sleeves from slipping along their respective sheaths 51 and 52. Rigid sleeve 83 provides a means for supporting O-rings 71 and 81 out of contact with sheath 51 and sleeve 84 similarly provides a means for supporting O-rings 72 and 82 out of contact with sheath 52, while lead 60 and extension 61 are being inserted into the sheaths. Raised ridges 91 and 92 are integrally formed in sheath 51, while raised ridges 93 and 94 are integrally formed in sheath 52. Raised ridges 91, 92, 93 and 94 comprise a means for preventing O-rings 71, 81, 72 and 82 respectively from slipping off their respective sheath ends.

As can be seen in the case of O-rings 71 and 81, the O-rings may be pushed up on sleeves 83 and 84 when they are not being used for assisting in holding the sheath ends about the lead end extension. O-rings 72 and 82 are shown rolled into place about ends 97 and 99 of sheath 52 respectively, thereby assisting in holding lead portion 55 and extension portion 57 respectively within the sheath 52. O-rings 71 and 81 are shown in ghost at 71a and 81a respectively in the position they will be rolled to after lead portion 54 and extension portion 56 respectively are inserted into sheath 51. In the embodiment shown, sleeves 83 and 84 are integrally formed in one unit having a central member 96 which connects the two sleeves.

The sheaths 14, 32, 51 and 52 in all the embodiments shown are made out of a material that is generally inert to body fluids, such as medical grade silicone rubber. By "generally inert to body fluids," it is meant that the material, under normal circumstances, and for a medically acceptable period of time will not react with body fluid so as to harm the body or seriously degrade the material. Likewise, support members 16, 67 and 68 are integrally molded, with their respective sheaths, out of the same material. Sleeves 83 and 84 and connecting members 96 may be made out of any material rigid enought to support an O-ring and which is generally inert to body fluids, for example Amidel ™ transparent nylon available from Union Carbide Corp., 270 Park Ave., N.Y., N.Y. Wires such as 15, 17, 65 and 66 may be made out of any suitable conducting material, and preferably a materal such as platinum, stainless steel or other conducting material which is generally inert to body fluids. Sleeves 62 and 63 are made out of stainless steel or any suitable metal or other material that may be crimped. The edges of the sheaths such as 97 and the edges of the sleeves 83 and 84 such as at 98 are rounded to prevent trauma to the tissues in which the connector is implanted. O-rings 71, 81, and 72 and 82 are made out of a material generally inert to body fluids, such as silicone rubber. Sutures 40 and 41 are made out of any suitable suture material, and preferably a material that does not degrade within the body such as silk.

It is a feature of the invention that the connector permits the length of lead and extensions within the body to be customized. The means for further compression of the sheath, such as suture 41 or O-ring 71, additionally serves to prevent the conditions necessary for such accidental removal.

A further feature of the invention is that the making of a connection with the connector according to the invention is very simple. Referring to FIG. 2, lead 10 only needs to be pushed onto one end of wire 17 and into the opening 33 of sheath 32, and likewise extension 11 only needs to be pushed onto the other end of wire 17 and into the other open end 34 of sheath 32. The friction force between surfaces such as 37 and 39 as the lead 10 enters sheath 32 will tend to compress sheath 32, thereby causing the opening 33 to enlarge, permitting the passing of lead 10 within sheath 32 until lead end 47 abuts on the surface 48 of support member 16. Thus, a positive connection is simply and immediately made without the need for the setting of screws, the adding of adhesive or any similar operation, and it is not necessary to wait for an adhesive to cure.

The positive fixation feature is another feature of the invention. Referring to FIG. 4 as an example, if the terminal such as lead 10 and the connector such as 30 are moved in directions tending to separate them, the frictional forces between surfaces 37 and 39 (at point 45) now tends to stretch sheath 32 causing it to contract about lead 10, and thus causing it to attach itself more strongly to lead 10, so that either the lead 10 or connector 30 will break before the grip of the sheath 32 is released. Thus, providing sheath 32 is sufficiently strong to resist breaking under the forces normally exerted on connector 30, sheath 32 will firmly hold to lead 10, under any such forces.

There has been described a novel connector that simplifies the connection of implantable electrical devices, reduces the bulk to be implanted, permits the customizing of lead and extension length and has numerous other advantages. While the invention has been described above in connection with particular embodiments, those skilled in the art will appreciate that the invention is not necessarily so limited, and that numerous other embodiments and departures from the embodiments shown may be made without departing from the inventive concepts. For example, although the invention has been described in connection with embodiments which may be used to connect a lead to an extension, it is contemplated that the connector according to the invention may be used to connect many types of electrical terminals and the end of a lead or extension is but one type of such a terminal. Although the connector has principally been described in terms of embodiments in which a pair of connections is made, the invention contemplates sheaths which may include three, four or N number of open ends which may be used to connect three, four or more terminals (leads). The invention contemplates also that the word "conductor" and phrase "means for making conductive connection" be taken in their broadest sense, i.e. any type of conduction. For example, the "conductor" may be an optic fiber which conducts a light beam and the "means for making conductive connection" may be a means for conducting the light beam through the conductor to the lead or other device to which the connector connects. As another example, sutures such as 41 may be used with bipolar leads while O-rings, such as 71 may be used with unipolar leads, while the stop such as 62 may be used in embodiments such as that shown in FIG. 2; these aspects have been simply combined in the manner shown for purposes of illustration, and have not been showed in combination with other embodiments so as to not necessarily multiply the number of figures. Other equivalent types of stops, conductive connectors, etc. may be used other than those shown. The various parts of the connectors, such as the sheaths, support members, the means for supporting the O-rings, etc. may take on many different sizes, shapes and configurations. For example, "Y" connections of "T" connections are within the practice of the invention. Additional features also may be added while employing the inventive elements. Those skilled in the art will also see many other variations of the invention.

What is claimed is:

1. A body implantable connector for connecting cut ends of a pair of body implantable leads, each lead including a helical conductor having a lumen, the helical conductor being encased in an insulator, the connector comprising:

sheath means made of a pliable rubber-like nonconductive material which is generally inert to body fluids, the sheath means being provided with a pair of open ends shaped for closely receiving cut ends of the leads and for frictionally fitting about the insulators of the leads in a generally fluid-tight connection, the material having sufficient strength to resist breaking under the forces normally exerted on the connector while implanted, but being sufficiently pliable to deform and so that the sheath means contracts about the leads under the frictional forces created between the sheath means and the insulators when the leads are urged in directions tending to separate them from the connector; and a wire means mounted in the sheath means and projecting within the open ends for mating in each lumen and including means for making conductive and mechanical connections between the helical conductors.

2. The connector of claim 1 further including a member, composed of the pliable material, integrally formed within the sheath means for mounting the wire means at its position to mate with the lumens.

3. The connector of claim 2 wherein the wire means has a bent portion lying at an angle to a longtiudinal axis of an unbent portion of the wire means.

4. The connector of claim 3 wherein the bent portion includes multiple bends which form an S-shaped configuration.

5. The connection of claim 1 further comprising means for compressing the sheath means about the leads after the leads are placed within the opening, thereby increasing frictional contact between the pliable material of the sheath means and the insulator of the lead.

6. The connector of claim 5 wherein the means for compressing includes at least one resilient O-ring mounted over the sheath means.

7. The connector of claim 6 further comprising a rigid sleeve mounted over the sheath means for supporting the O-ring in a stretched condition out of contact with the sheath means while leads are being inserted in the sheath means.

8. The connector of claim 5 wherein the means for compressing includes a suture around the sheath means.

* * * * *

UNITED STATES PATENT AND TRADEMARK OFFICE
CERTIFICATE OF CORRECTION

PATENT NO. : 4,411,276
DATED : October 25, 1983
INVENTOR(S) : Eugene A. Dickhudt, Roger A. Paulson It is certified that error appears in the above-identified patent and that said Letters Patent are hereby corrected as shown below:

Column 1,
　Line 51, insert --and-- between "pin" and "socket";

Column 2,
　Line 22, "feature" should be --factors--;

Column 5,
　Line 16, "noted" should be --mated--;

Column 6,
　Line 11, "64" should be --84--;

Column 8,
　Line 51, "connection" should be --connector--.

Signed and Sealed this

Seventh Day of August 1984

[SEAL]

Attest:

GERALD J. MOSSINGHOFF

Attesting Officer

Commissioner of Patents and Trademarks